(12) United States Patent
Pan

(10) Patent No.: US 8,846,381 B2
(45) Date of Patent: Sep. 30, 2014

(54) BIOGAS DESULFURIZATION DEVICE

(75) Inventor: Wenzhi Pan, Beijing (CN)

(73) Assignee: Beijing Helee Bio-Energy Technology Co., Ltd., Beijing (CN)

( * ) Notice: Subject to any disclaimer, the term of this patent is extended or adjusted under 35 U.S.C. 154(b) by 630 days.

(21) Appl. No.: 13/091,862

(22) Filed: Apr. 21, 2011

(65) Prior Publication Data

US 2012/0270307 A1 Oct. 25, 2012

(51) Int. Cl.
*C12M 1/04* (2006.01)
*C12M 1/107* (2006.01)
*C12M 1/00* (2006.01)

(52) U.S. Cl.
CPC ............... *C12M 21/04* (2013.01); *C12M 47/18* (2013.01); *Y02E 50/343* (2013.01)
USPC ..................... 435/294.1; 435/266; 435/299.1; 435/300.1

(58) Field of Classification Search
CPC ...... C12M 21/04; C12M 47/18; C12M 23/58; C12M 25/18; C12M 29/06; B01D 53/52; B01D 53/84
USPC .................................... 435/266, 299.1, 300.1
See application file for complete search history.

(56) References Cited

U.S. PATENT DOCUMENTS

2010/0261266 A1* 10/2010 Nagamori et al. ......... 435/300.1
2011/0318778 A1* 12/2011 Petersen et al. ................. 435/41

FOREIGN PATENT DOCUMENTS

| JP | 2002079051 A | * | 3/2002 |
| JP | 2003062421 A | * | 3/2003 |
| JP | 2008208355 A | * | 9/2008 |

OTHER PUBLICATIONS

English language machine translation of JP-2008208355 (Sep. 2008), pp. 1-15.*

* cited by examiner

Primary Examiner — William H Beisner
(74) Attorney, Agent, or Firm — J.C. Patents

(57) ABSTRACT

A biogas desulfurization device comprises an anaerobic system, a desulfurization liquid circulating system, an oxygen supply device and a desulfurization system, wherein the anaerobic system is used for generating biogas and filling the generated biogas into the desulfurization system, the desulfurization liquid circulating system is used for filling the desulfurization liquid into the desulfurization system and recycling the desulfurization liquid that has undergone the desulfurization operation, the oxygen supply device is used for filling air into the desulfurization system, and the desulfurization system which comprises at least one stage desulfurization tower group is used for carrying out the desulfurization operation on the biogas from the anaerobic system, the desulfurization operation is conducted by the desulfurization liquid received from the desulfurization liquid circulating system in an aerobic environment. The biogas desulfurization device can reduce the amount of hydrogen sulfide in the biogas to less than 10 ppm while eliminating secondary pollution.

5 Claims, 1 Drawing Sheet

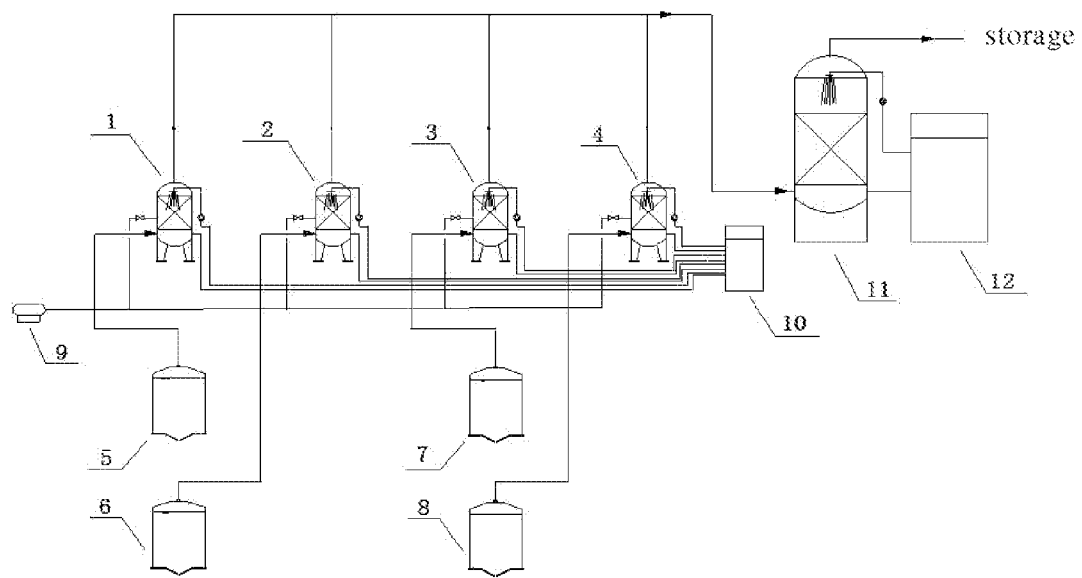

BIOGAS DESULFURIZATION DEVICE

FIELD OF THE TECHNOLOGY

The invention belongs to the field of chemical desulfurization, particularly relates to a biogas desulfurization device.

BACKGROUND

Biogas is a novel energy resource that our country is vigorously developing at present. Organic materials such as industrial wastewater, plant stalks, animal wastes and the like are decomposed and metabolized under certain moisture, temperature and anaerobic conditions by a variety and large number of microbes with different functions to finally form a gaseous mixture of methane, carbon dioxide, etc., i.e., biogas. This is a complex biochemical process. A large quantity of hydrogen sulfide can be generated along with the generation of biogas. Hydrogen sulfide is a toxic gas, and will cause adverse reactions of human bodies if inhaled, and may endanger human life. Besides, hydrogen sulfide can corrode pipelines and combustion equipment under aerobic, wet and hot conditions. Therefore, many researchers are dedicated to the study of the biogas desulfurization technology. Technologies that can be used in industry scale at present are usually physical and chemical technologies, including the conventional physical and chemical technologies such as direct gas stripping, oxidation, chemical precipitation and the like. Although these physical and chemical processes can achieve good effects, the energy consumption, chemical agents and operating cost are relatively high, and the secondary pollution exists.

SUMMARY

I. Technical Problem to Be Solved

The object of the invention is to overcome the disadvantages in the present physical and chemical process, and provide a biogas desulfurization device based on microbe desulfurization process, which can lower investment and operating costs, reduce energy consumption and effectively control environmental pollution.

II. Technical Solution

In order to realize the above object, the present invention provides a biogas desulfurization device which comprises an anaerobic system, a desulfurization liquid circulating system, an oxygen supply device and a desulfurization system;

the anaerobic system is used for generating biogas and filling the generated biogas into the desulfurization system;

the desulfurization liquid circulating system is used for filling desulfurization liquid into the desulfurization system and recycling the desulfurization liquid which has undergone the desulfurization operation;

the oxygen supply device is used for filling air into the desulfurization system;

the desulfurization system which comprises at least one stage desulfurization tower group is used for carrying out the desulfurization operation on biogas coming from the anaerobic system. The desulfurization operation is conducted by desulfurization liquid received from the desulfurization liquid circulating system in an aerobic environment formed after the air has been filled by the oxygen supply device.

The anaerobic system comprises at least one anaerobic digester, the number of the anaerobic digesters is corresponding to the number of the desulfurization towers in the first stage desulfurization tower group of the desulfurization system;

each of the anaerobic digesters is correspondingly being connected to one of the desulfurization towers of the first stage desulfurization tower group so as to supply the biogas to the desulfurization towers.

The desulfurization system comprises two stages desulfurization tower groups, the first stage desulfurization tower group comprises four desulfurization towers, and the second stage desulfurization tower group comprises one desulfurization tower.

The desulfurization tower comprises a gas inlet, a gas outlet, a desulfurization liquid inlet, a desulfurization liquid outlet and an internal filler;

the gas inlet and the desulfurization liquid outlet are arranged at the bottom part of the desulfurization tower, and the gas outlet and the desulfurization liquid inlet are arranged at the top part of the desulfurization tower.

The gas outlets of the four desulfurization towers of the first stage desulfurization tower group are connected with each other and then connected to the gas inlet of the desulfurization tower of the second stage desulfurization tower group.

The desulfurization liquid circulating system comprises a desulfurization liquid tank, a circulating pump and a spraying device;

the circulating pump is used for drawing desulfurization liquid from the desulfurization liquid tank and supplying the desulfurization liquid to the spraying device;

the spraying device is arranged at the position of the desulfurization liquid inlet, and is used for filling the desulfurization liquid into the desulfurization tower.

The desulfurization liquid outlet is connected to the desulfurization liquid tank so as to recycle the desulfurization liquid which has undergone the desulfurization operation to the desulfurization liquid circulating system.

The oxygen supply device comprises an air compressor and a throttle valve;

the air compressor is used for filling the air into the desulfurization tower;

the throttle valve is used for controlling the amount of air filled in the desulfurization tower.

III. Technical Effect

The biogas desulfurization device based on microbe desulfurization process provided in the present invention carries out biogas desulfurization operation by using the microbe desulfurization process, and the microbe desulfurization process has the following advantages compared to the present conventional physical and chemical desulfurization process: (1) no catalyst is required, no other oxidants is required except for air; (2) energy consumption is low; (3) no chemical sludge is produced; (4) hydrogen sulfide becomes raw materials in the self-circulating process of biological desulfurization; (5) high efficiency of sulfide removing and high reaction speed are achieved. The biogas desulfurization device is simple and convenient for operation, and the amount of hydrogen sulfide can be more efficiently reduced through repeated desulfurization operation, the secondary pollution can be eliminated through self-circulation and metabolization of microbes. Specifically, by using the biogas desulfurization device, the amount of hydrogen sulfide in biogas can be reduced to less than 10 ppm from 2,000-3,000 ppm after the desulfurization.

BRIEF DESCRIPTION OF THE DRAWING(S)

The FIGURE is a structural schematic diagram for the biogas desulfurization device provided in the technical solution of the invention;

1: first desulfurization tower; 2: second desulfurization tower; 3: third desulfurization tower; 4: fourth desulfurization tower; 5: first anaerobic digester; 6: second anaerobic digester; 7: third anaerobic digester; 8: fourth anaerobic digester; 9: oxygen supply device; 10: first desulfurization liquid circulating system; 11: second desulfurization tower group; 12: second desulfurization liquid circulating system.

DETAILED DESCRIPTION

The purpose, content and advantages of present invention is described in detail below by way of embodiments with reference to the accompanying drawings. The following embodiments are used for more clearly describing the invention, but should not be used for limiting the scope of the invention.

Structural characteristics and the operating process of the biogas desulfurization device provided by the present invention are described in detail in the embodiment.

As shown in The FIGURE, the biogas desulfurization device comprises an anaerobic system, a desulfurization liquid circulating system, an oxygen supply device and a desulfurization system;

the anaerobic system is used for generating biogas and filling the generated biogas into the desulfurization system;

the desulfurization liquid circulating system is used for filling the desulfurization liquid into the desulfurization system and recycling the desulfurization liquid which has undergone the desulfurization operation; the desulfurization liquid contains a large quantity of biological bacterias, including various of desulfurization bacterias such as filamentous sulfur bacteria, photosynthetic sulfur bacteria, colorless sulfur bacteria, etc.; and self-circulating metabolization is conducted among the different kinds of microbes. Liquid effluent after being precipitated and filtered is added into the circulating water of the desulfurization tower; microbes in the liquid effluent need to absorb hydrogen ions to finish the metabolization, which is beneficial for the removing of hydrogen sulfide.

The oxygen supply device 9 is used for filling air into the desulfurization system, e.g. filling oxygen into the desulfurization system so as to create the survival conditions for desulfurization bacteria.

The desulfurization system which comprises at least one stage desulfurization tower group is used for carrying out the desulfurization operation on biogas from the anaerobic system, the desulfurization operation is conducted by desulfurization liquid received from the desulfurization liquid circulating system in an aerobic environment formed after the air has been filled by the oxygen supply device 9.

The anaerobic system comprises at least one anaerobic digester, the number of the anaerobic digesters is corresponding to the number of desulfurization towers in the first stage desulfurization tower group of the desulfurization system;

each of the anaerobic digesters 5, 6, 7 and 8 is correspondingly being connected to a desulfurization tower of the first stage desulfurization tower group so as to supply the biogas to the desulfurization tower; and each anaerobic digester can generate 200 m³ of biogas per hour.

The desulfurization system comprises two stages desulfurization tower groups, the first stage desulfurization tower group comprises four desulfurization towers 1, 2, 3 and 4, and the second stage desulfurization tower group 11 comprises one desulfurization tower.

The desulfurization tower comprises a gas inlet, a gas outlet, a desulfurization liquid inlet, a desulfurization liquid outlet and an internal filler;

the gas inlet and the desulfurization liquid outlet are arranged at the bottom part of the desulfurization tower, and the gas outlet and the desulfurization liquid inlet are arranged at the top part of the desulfurization tower;

the internal filler on which a large quantity of biological desulfurization bacteria is adhered is a flocculent filler and is hung inside the desulfurization tower from the top of the tower to the bottom of the tower.

The gas outlets of the four desulfurization towers of the first stage desulfurization tower group are connected with each other and then connected to the gas inlet of the desulfurization tower of the second stage desulfurization tower group; the desulfurization tower of the second stage desulfurization tower group is used for carrying out further desulfurization on the biogas that has undergone the desulfurization in the first stage desulfurization tower group so as to achieve better effect.

The desulfurization liquid circulating systems 10 and 12 respectively comprises a desulfurization liquid tank, a circulating pump and a spraying device, and are used for filling the desulfurization liquid into the desulfurization towers to contact with the biogas;

the circulating pump is used for drawing the desulfurization liquid from the desulfurization liquid tank and supplying the desulfurization liquid to the spraying device;

the spraying device is arranged at the position of the desulfurization liquid inlet, and is used for filling the desulfurization liquid into the desulfurization tower.

The desulfurization liquid outlet is connected to the desulfurization liquid tank so as to recycle desulfurization liquid that has undergone the desulfurization operation to the desulfurization liquid circulating system.

the oxygen supply device comprises an air compressor and a throttle valve;

the air compressor is used for filling the air into the desulfurization tower;

the throttle valve is used for controlling the amount of air filled in the desulfurization tower, wherein the amount of oxygen is usually not more than 2%.

The following is the detail description of the desulfurization operating process of the biogas desulfurization device provided in the present invention:

Step 1, connecting each of the anaerobic digesters 5, 6, 7 and 8 of desulfurization tower of the first stage desulfurization tower group, and respectively filling the biogas into the corresponding desulfurization towers 1, 2, 3 and 4, and meanwhile the oxygen supply device 9 fills air into each of the desulfurization towers to form aerobic environment;

Step 2, the biogas is filled from the gas inlets at the bottom part of the desulfurization towers 1, 2, 3 and 4 of the first stage desulfurization tower group; meanwhile, the circulating pump of the circulating desulfurization liquid system 10 draws desulfurization liquid from the desulfurization liquid tank, and the spraying device fills the desulfurization liquid into the desulfurization towers from the desulfurization liquid inlets at the top part of the desulfurization towers;

Step 3, the desulfurization liquid moves from top to bottom in the desulfurization towers, and fully contacts with the biogas while the biogas moves from bottom to top in the desulfurization towers, thereby achieving good desulfurization effect;

wherein reaction $H_2S+O_2=H_2O+SO_2$ occurs under the condition of sufficient oxygen, and reaction $2H_2S+O_2=2H_2O+2S$ occurs under the condition of insufficient oxygen;

Step 4, the desulfurization liquid that has undergone the desulfurization operation is flowing out from an outlet of the desulfurization tower and filled into the desulfurization liquid tank; meanwhile, the biogas is led out from the gas outlet at top part of the desulfurization tower and mixed with the biogas leading out of the rest of the desulfurization towers of the first stage desulfurization tower group after desulfurization and then the mixed biogas is filled into the second stage desulfurization tower group 11;

Step 5, Steps 2 and 3 are repeated on the filled biogas in the second stage desulfurization tower group, when the expected desulfurization effect is achieved, the obtained biogas is stored, finishing the desulfurization process.

The biogas desulfurization device based on microbe desulfurization process provided in the invention carries out biogas desulfurization operation by using the microbe desulfurization process, and the microbe desulfurization process has the following advantages compared to the present conventional physical and chemical desulfurization process: (1) no catalyst is required, no other oxidants is required except for air; (2) energy consumption is low; (3) no chemical sludge is produced; (4) hydrogen sulfide becomes raw materials in the self-circulating process of biological desulfurization; (5) high efficiency of sulfide removing of sulfide and high reaction speed are achieved. The biogas desulfurization device is simple and convenient for operation, and the amount of hydrogen sulfide can be more efficiently reduced through repeated desulfurization operation, the secondary pollution can be eliminated through self-circulation and metabolization of microbes. Specifically, by using the biogas desulfurization device, the amount of hydrogen sulfide in biogas can be reduced to less than 10 ppm from 2,000-3,000 ppm after the desulfurization.

The above are just the preferable embodiments of the invention. It should be pointed out that improvements and variations can be made based on the technical principle of the invention by a person skilled in the technical field, thus the improvements and variations also should be regarded as within the scope of the invention.

What is claimed is:

1. A biogas desulfurization device, characterized in that the device comprises a desulfurization system, an oxygen supply device, an anaerobic system, and a desulfurization liquid circulating system;

the desulfurization system comprises two stages desulfurization tower groups, a desulfurization tower comprises a gas inlet, a gas outlet, a desulfurization liquid inlet, a desulfurization liquid outlet, and an internal filler, the gas inlet and the desulfurization liquid outlet are arranged at the bottom part of the desulfurization tower, the gas outlet and the desulfurization liquid inlet are arranged at the top part of the desulfurization tower, the first stage desulfurization tower group comprises four desulfurization towers, and the second stage desulfurization tower group comprises one desulfurization tower, the gas outlets of the four desulfurization towers of the first stage desulfurization tower group are connected with each other and then connected to a gas inlet of the desulfurization tower of the second stage desulfurization tower group;

the oxygen supply device is connected to the desulfurization tower and used for filling air into the desulfurization system, the oxygen supply device comprises an air compressor and a throttle valve, the air compressor is used for filling air into the desulfurization tower, the throttle valve is used for controlling the amount of the air filled in the desulfurization tower;

the anaerobic system is used for generating biogas and filling the generated biogas into the desulfurization system through the gas inlet, the anaerobic system comprises at least one anaerobic digester;

the desulfurization liquid circulating system is used for filling desulfurization liquid into the desulfurization tower and recycling the desulfurization liquid that has undergone the desulfurization operation to the desulfurization liquid circulating system, the desulfurization liquid circulating system comprises a desulfurization liquid tank connected to the desulfurization liquid outlet and containing the desulfurization liquid, a circulating pump connected to the desulfurization liquid tank, and a spraying device arranged at the top part of the desulfurization tower, the spraying device is connected to the circulating pump through the desulfurization liquid inlet and used for filling the desulfurization liquid into the desulfurization tower;

the desulfurization liquid comprises biological bacterias which can utilize hydrogen sulfide as raw materials for self-circulating process of biological desulfurization;

the desulfurization tower is used for carrying out the desulfurization operation on the biogas from the anaerobic system, the desulfurization operation is conducted by the desulfurization liquid received from the desulfurization liquid circulating system in an aerobic environment formed after the air has been filled by the oxygen supply device.

2. The biogas desulfurization device according to claim 1, characterized in that the number of the anaerobic digesters is corresponding to the number of desulfurization towers in the first stage desulfurization tower group of the desulfurization system;

each of the anaerobic digesters is correspondingly being connected to one of the desulfurization towers in the first stage desulfurization tower group so as to supply the biogas to the desulfurization towers.

3. The biogas desulfurization device according to claim 1, characterized in that the biological bacterias comprised in the desulfurization liquid including desulfurization bacterias selected from filamentous sulfur bacteria, photosynthetic sulfur bacteria and colorless sulfur bacteria.

4. The biogas desulfurization device according to claim 1, characterized in that the internal filler is a flocculent filler and hung inside the desulfurization tower from the top of the tower to the bottom of the tower, and on which biological desulfurization bacterias are adhered.

5. The biogas desulfurization device according to claim 4, characterized in that the biological desulfurization bacterias are selected from filamentous sulfur bacteria, photosynthetic sulfur bacteria and colorless sulfur bacteria.

* * * * *